US010500383B2

(12) United States Patent
Lin et al.

(10) Patent No.: US 10,500,383 B2
(45) Date of Patent: Dec. 10, 2019

(54) GRANULE DELIVERY SYSTEM AND METHOD OF DELIVERING GRANULES USING THE SAME

(71) Applicant: JTI Biomed Corp., Tainan (TW)

(72) Inventors: Jiin-Huey Chern Lin, Winnetka, IL (US); Chien-Ping Ju, Kansas City, MO (US)

(73) Assignee: JTI BIOMED CORP., Tainan (TW)

( * ) Notice: Subject to any disclaimer, the term of this patent is extended or adjusted under 35 U.S.C. 154(b) by 38 days.

(21) Appl. No.: 15/326,374

(22) PCT Filed: Jul. 10, 2015

(86) PCT No.: PCT/US2015/039852
§ 371 (c)(1),
(2) Date: Jan. 13, 2017

(87) PCT Pub. No.: WO2016/010836
PCT Pub. Date: Jan. 21, 2016

(65) Prior Publication Data
US 2017/0209680 A1    Jul. 27, 2017

Related U.S. Application Data

(60) Provisional application No. 62/025,140, filed on Jul. 16, 2014.

(51) Int. Cl.
*A61M 5/31* (2006.01)
*A61M 31/00* (2006.01)
*A61M 5/315* (2006.01)

(52) U.S. Cl.
CPC ........ *A61M 31/007* (2013.01); *A61M 5/3129* (2013.01); *A61M 5/3137* (2013.01); *A61M 5/31511* (2013.01); *A61M 2005/3142* (2013.01); *A61M 2210/02* (2013.01)

(58) Field of Classification Search
CPC .............. A61M 31/007; A61M 5/3137; A61M 5/31511; A61M 2005/3142; A61M 2210/02
See application file for complete search history.

(56) References Cited

U.S. PATENT DOCUMENTS

| 5,346,475 | A | * | 9/1994 | Gregorio | ............. | A61M 5/3271 |
| | | | | | | 604/110 |
| 5,762,633 | A | * | 6/1998 | Whisson | ................ | A61M 5/28 |
| | | | | | | 604/187 |
| 5,891,104 | A | * | 4/1999 | Shonfeld | ................ | A61M 5/46 |
| | | | | | | 604/195 |
| 5,910,315 | A | | 6/1999 | Stevenson et al. | | |
| 6,554,803 | B1 | | 4/2003 | Ashman | | |
| 2006/0052794 | A1 | | 3/2006 | McGill et al. | | |
| 2006/0116642 | A1 | | 6/2006 | Bills | | |
| 2007/0071791 | A1 | * | 3/2007 | Fischer | ................... | A61L 27/32 |
| | | | | | | 424/423 |

* cited by examiner

*Primary Examiner* — Lauren P Farrar
(74) *Attorney, Agent, or Firm* — Bacon & Thomas, PLLC (57) ABSTRACT

A granule delivery system contains a plunger and a divided tube, wherein the divided tube has two or more partial shells which are suitable to be coupled to each other, so that a longitudinal channel is formed in the divided tube, each of the partial shells is able to move longitudinally in relation to the other, and the plunger is able to be inserted into the longitudinal channel, when the two or more partial shells are coupled to each other.

9 Claims, 15 Drawing Sheets

GRANULE DELIVERY SYSTEM AND METHOD OF DELIVERING GRANULES USING THE SAME

FIELD OF THE INVENTION

The present invention is related to a technique for delivering granules, in particular porous granules, into a bone cavity, for enhancing bone ingrowth.

BACKGROUND OF THE INVENTION

Figure 1:
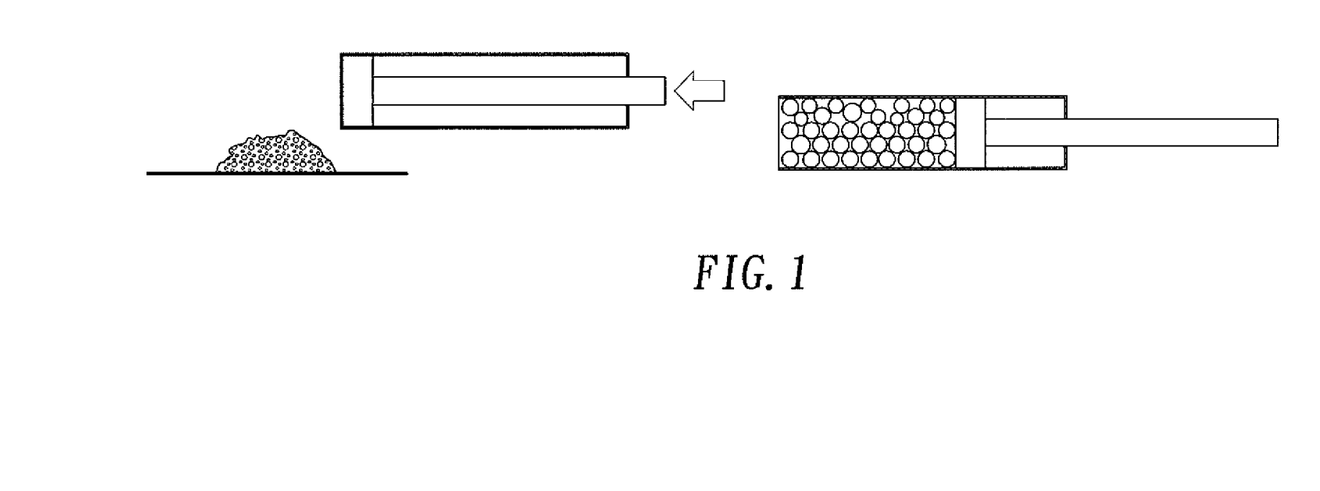
FIG. 1 are schematic cross-sectional views from right to left showing the result of using the conventional syringe to deliver porous granules, wherein the arrow represents the advance of the plunger.

The conventional syringe is designed for delivering liquid, or sometimes paste. When the conventional syringe is used to deliver granules, in particular fragile porous granules, into a bone cavity, for enhancing bone ingrowth, the frictions created between the surfaces of the granules themselves and between the surfaces of the granules and the inner surface of a barrel of the syringe and a thin tube connecting the barrel to the bone cavity are often too large to successfully complete the delivery, especially when the granules are porous granules which would be crushed by the friction, as shown in FIG. 1. More friction will be created once the porous granules start crushing and the delivery is often aborted due to undue large friction.

SUMMARY OF THE INVENTION

Figure 2:
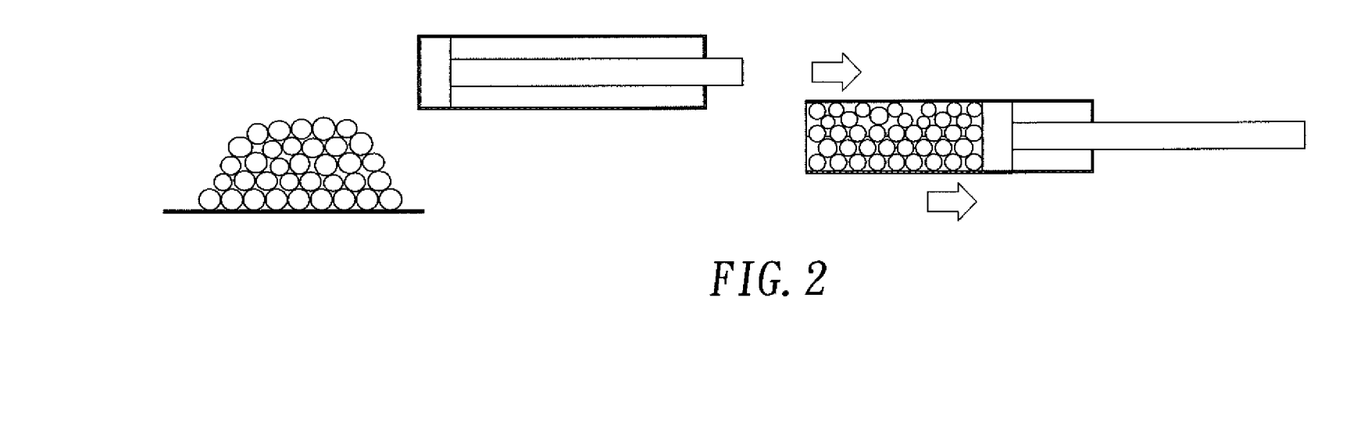
FIG. 2 are schematic cross-sectional views from right to left showing the result of using a new measure provided in the present invention to deliver porous granules, wherein the arrows represent that the two half shells of the divided tube are withdrawn alternately.

The gist of the present invention is to provide a new measure to solve the aforesaid delivery puzzle. As an example shown in FIG. 2, the new measure provided in the present invention utilizes a divided tube composed of two half shells and a plunger, wherein the granules are held steady by the plunger while the two half shells of the divided tube are withdrawn one at a time, so that granules originally in the divided tube are exposed gradually from a distal end thereof, and thus fall from the divided tube. Apparently, the measure provided in the present invention is able to deliver the granules with a minimum possible friction being created, and to successfully deliver porous granules without crushing them.

A granule delivery system constructed according to the present invention comprises a plunger; and a divided tube, wherein the divided tube comprises two or more partial shells which are adapted to be coupled to each other, so that a longitudinal channel is formed in the divided tube, each of the partial shell is able to move longitudinally in relation to the other, and said plunger is adapted to be inserted into said longitudinal channel, when said two or more partial shells are coupled to each other.

Preferably, said two or more partial shells are two half shells.

Preferably, the granule delivery system of the present invention further comprises a holder, wherein the divided tube are adapted to be slidably held by said holder, and the partial shells of the divided tube held by said holder are able to move longitudinally in relation to said holder.

Preferably, the granule delivery system of the present invention further comprises an engaging means for allowing the longitudinal movement between the partial shells and the holder only in one direction. More preferably, said engaging means comprises an elastic clip provided on each of said partial shells, and a series of parallel detents corresponding to said elastic clip provided on the holder at a regular interval longitudinally, so that the elastic clip is ratchetingly engaged with the series of parallel detents.

Preferably, the granule delivery system of the present invention further comprises granules adapted to be introduced into the longitudinal channel.

The present invention further provides a method of delivering granules into a space comprising the following steps: a) preparing the granule delivery system of the present invention; b) introducing granules into the longitudinal channel formed in the divided tube; c) inserting the plunger into the channel of the divided tube so that the plunger contacts the granules; and d) withdrawing said two or more partial shells at the same time or one-by-one to expose the granules from the divided tube.

The method of the present invention preferably further comprises repeating the withdrawing in step d), so that more granules in the divided tube are exposed from the divided tube.

Preferably, the method of the present invention further comprises e) moving the divided tube so that the divided tube is separated from the exposed granules.

BRIEF DESCRIPTION OF THE DRAWINGS

FIG. 5a to FIG. 5d show a GDS constructed according to a third preferred embodiment of the present invention, wherein FIG. 5a and FIG. 5b are views from two opposite sides.

DETAILED DESCRIPTION OF THE INVENTION

Figure 3A:
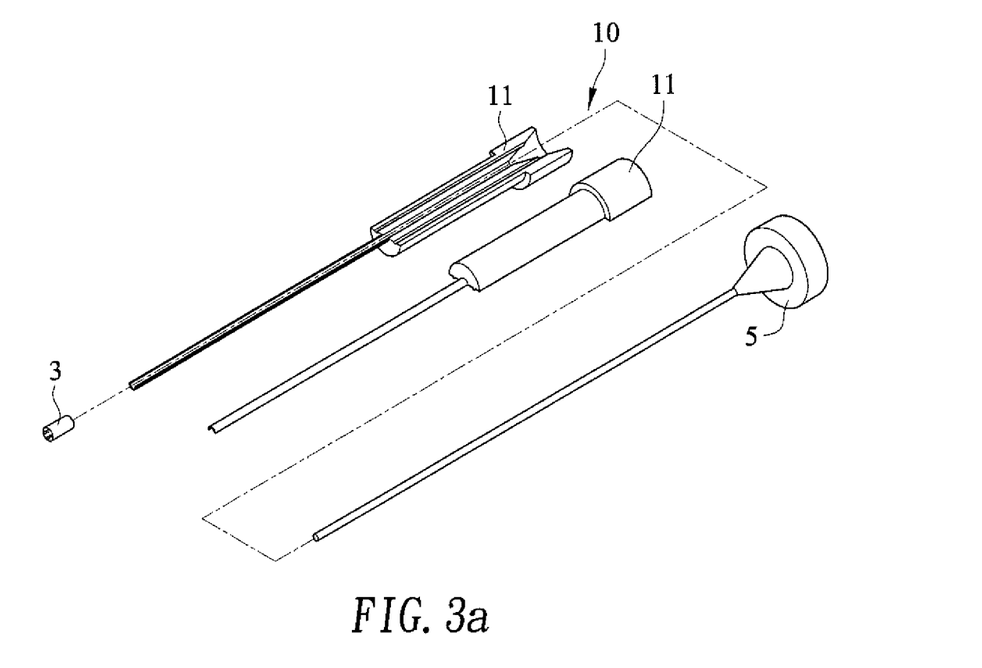
FIG. 3a and FIG. 3b are perspective views showing a granule delivery system (hereinafter abbreviated as GDS) constructed according to a first preferred embodiment of the present invention.
Figure 3B:
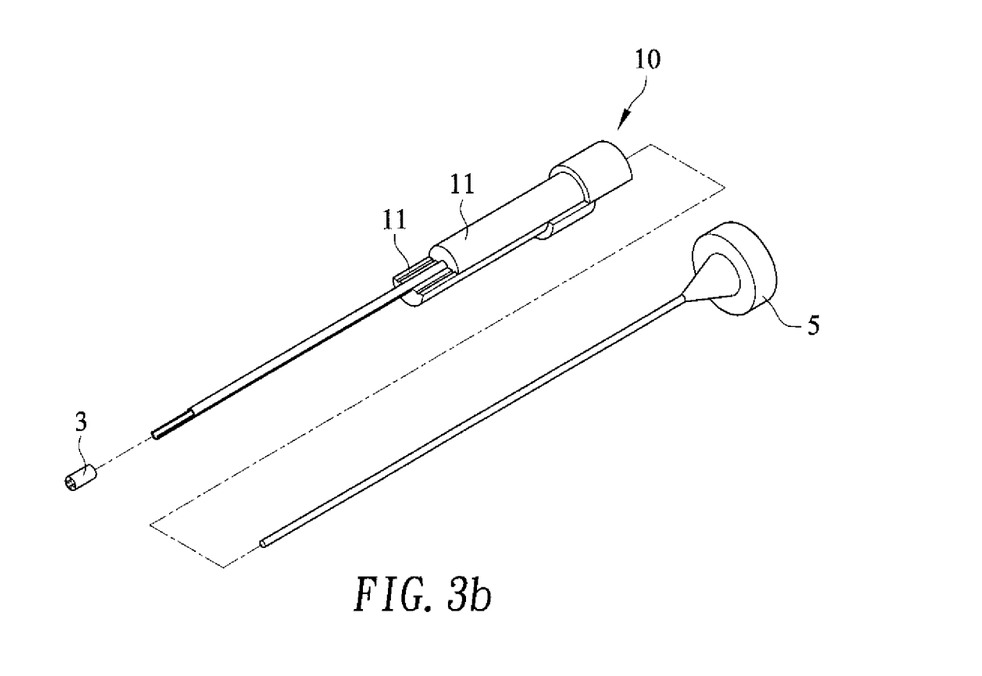

A granule delivery system (hereinafter abbreviated as GDS) constructed according to a first preferred embodiment of the present invention is shown in FIG. 3a and FIG. 3b, wherein the GDS comprises a divided tube 10 composed of two half shells 11, a plunger 5 and a perforated cap 3. The half shells have an enlarged proximal end to facilitate the coupling thereof and sliding movement relatively to each other after the coupling. The perforated cap 3 is used to hold porous granules (not shown in FIGS. 3a and 3b) in a longitudinal channel formed in the divided tube 10 after the coupling, and allow the porous granules to be wet by liquid (e.g. blood) through perforations formed on the perforated cap 3. The plunger 5 is not inserted into the divided tube 10 deeply but to an extent so that its front end contacts the porous granules filled in the longitudinal channel of the divided tube 10, and thus the filled granules are stopped by the plunger 5 while the two half shells 11 of the divided tube 10 are withdrawn one at a time, thereby the porous granules originally in the divided tube are exposed gradually from a distal end thereof, and fall from the divided tube. The alternate retreat of the two half shells 11 of the divided tube 10 are repeated, until all the filled granules in the divided tube fall.

Figure 4A:
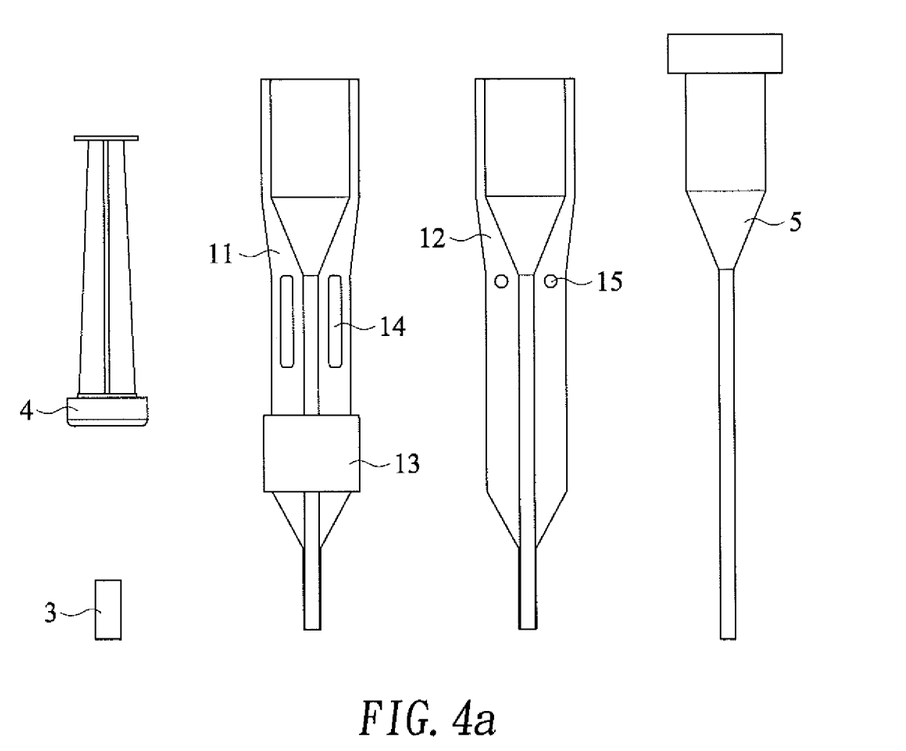
FIG. 4a to FIG. 4d are planar and perspective views showing a GDS constructed according to a second preferred embodiment of the present invention.
Figure 4B:
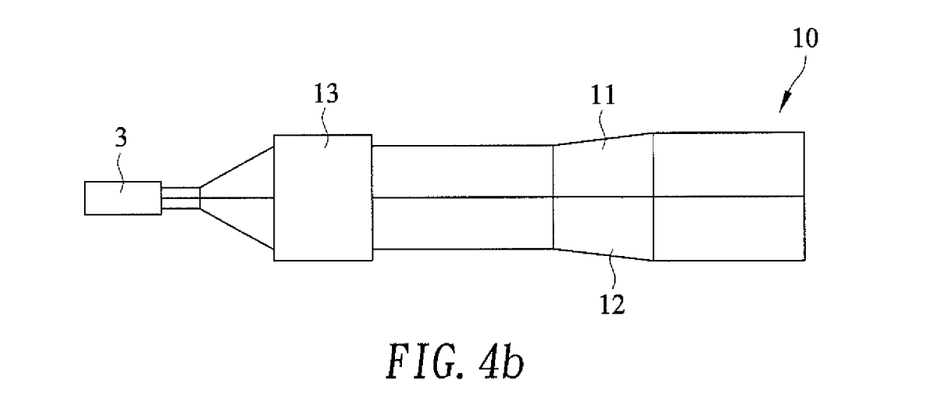
Figure 4C:
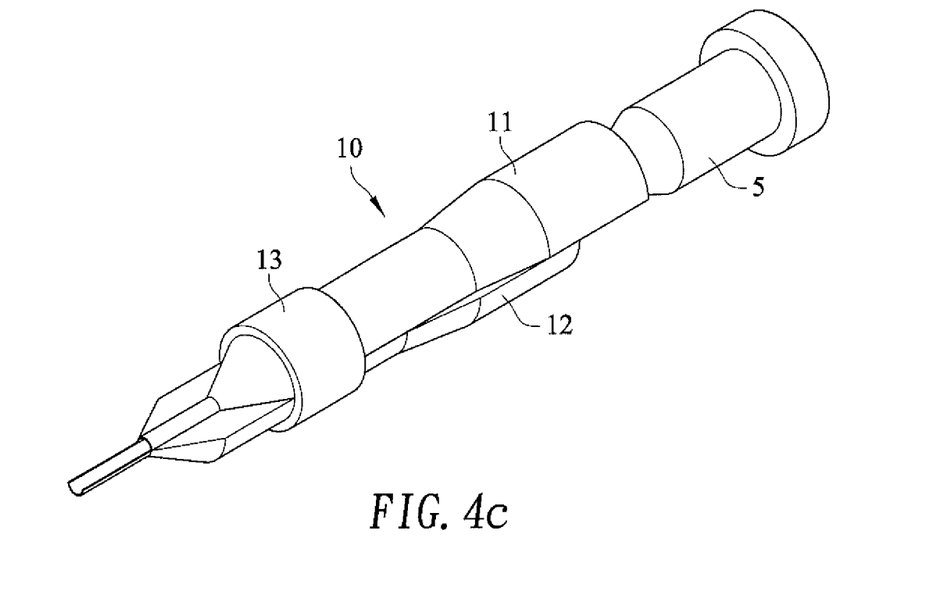
Figure 4D:
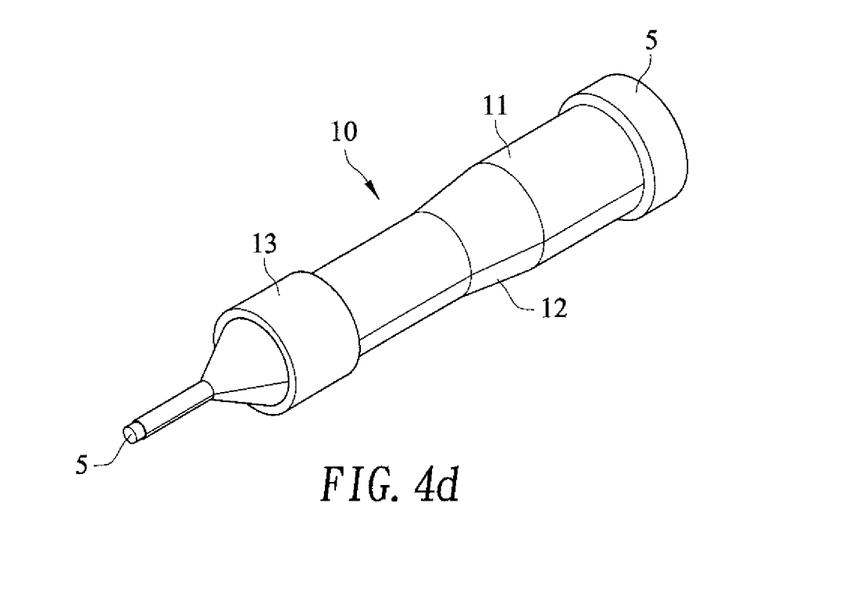
Figure 5A:
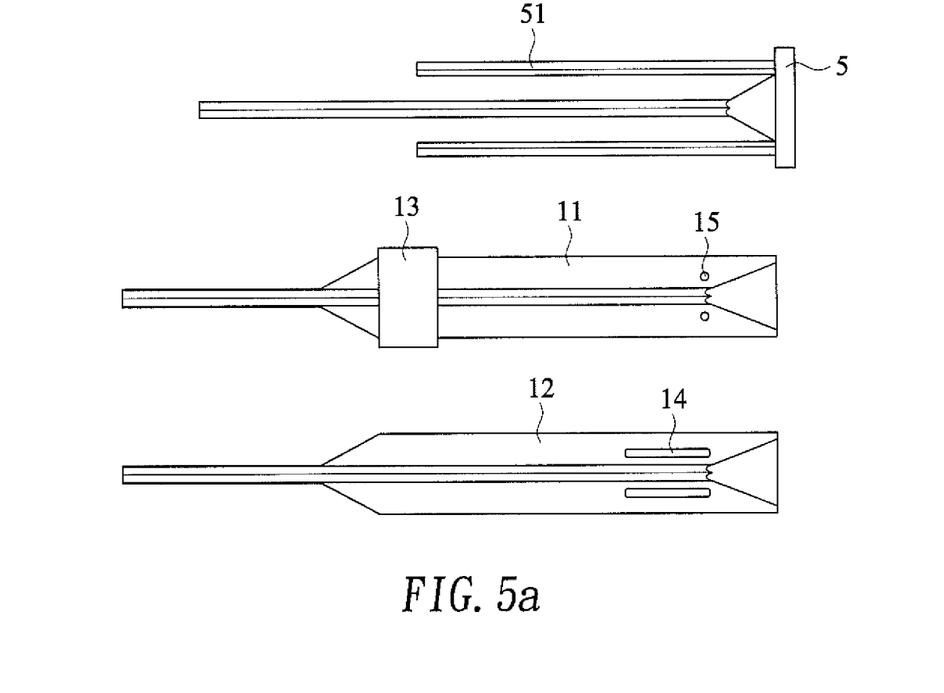
Figure 5B:
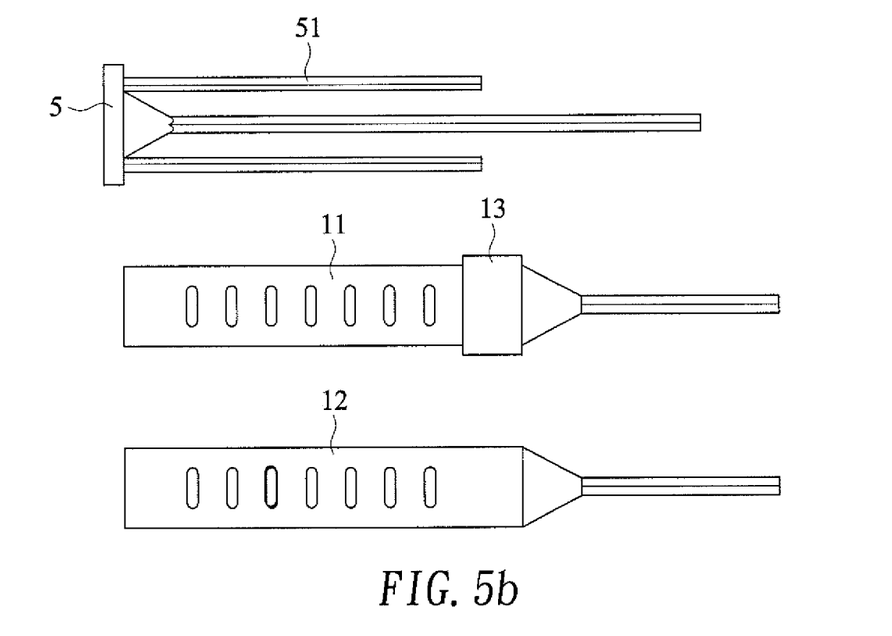
Figure 5C:
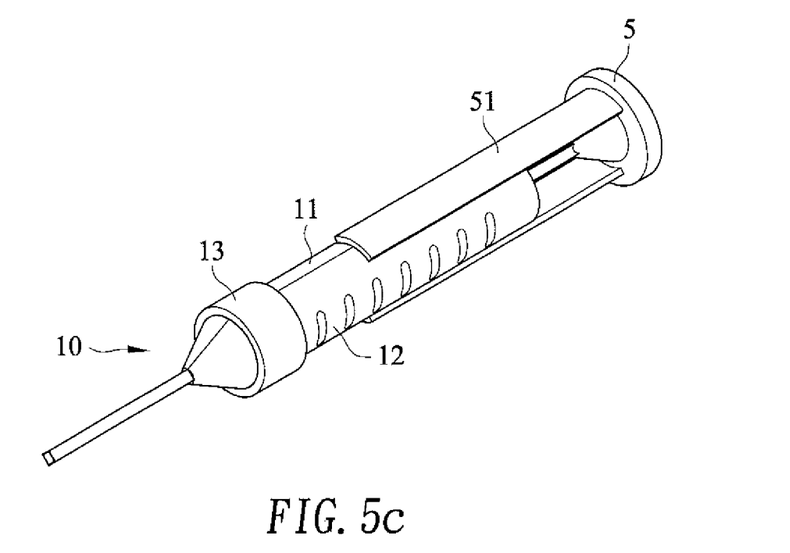
FIG. 5c is a perspective view of the GDS being assembled.
Figure 5D:
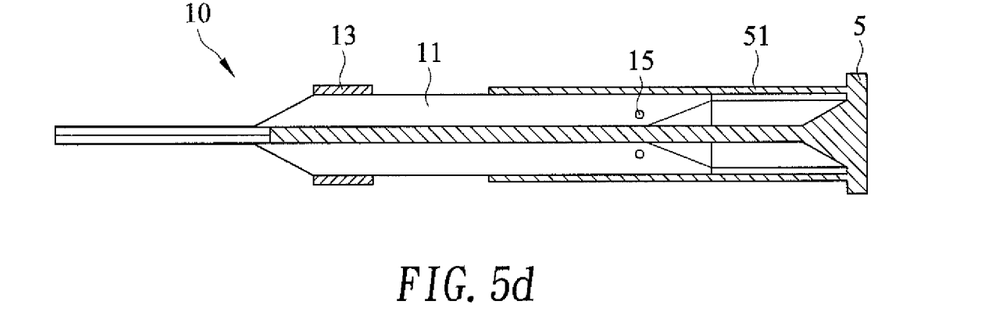
FIG. 5d is a cross-sectional view of the assembled GDS.
Figure 6A:
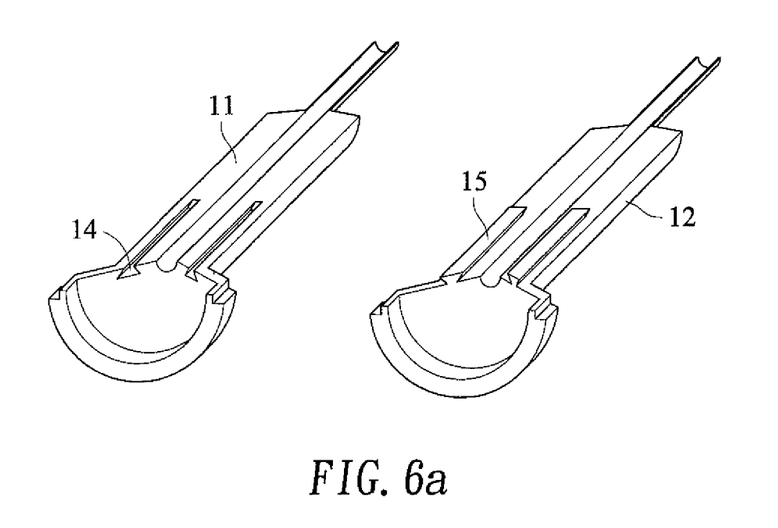
FIG. 6a to FIG. 6d are perspective and planar views showing a GDS constructed according to a fourth preferred embodiment of the present invention.
Figure 6B:
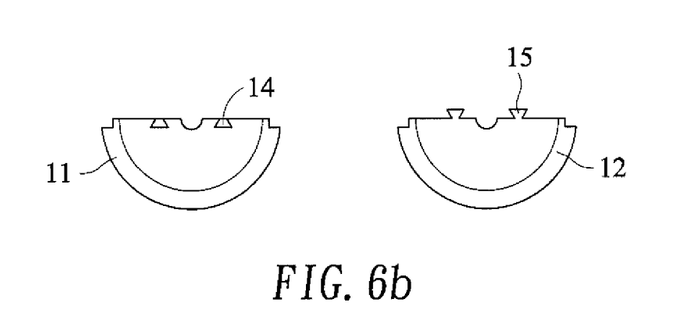
Figure 6C:
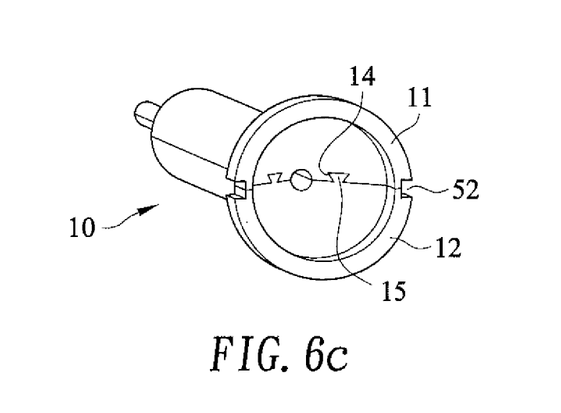
Figure 6D:
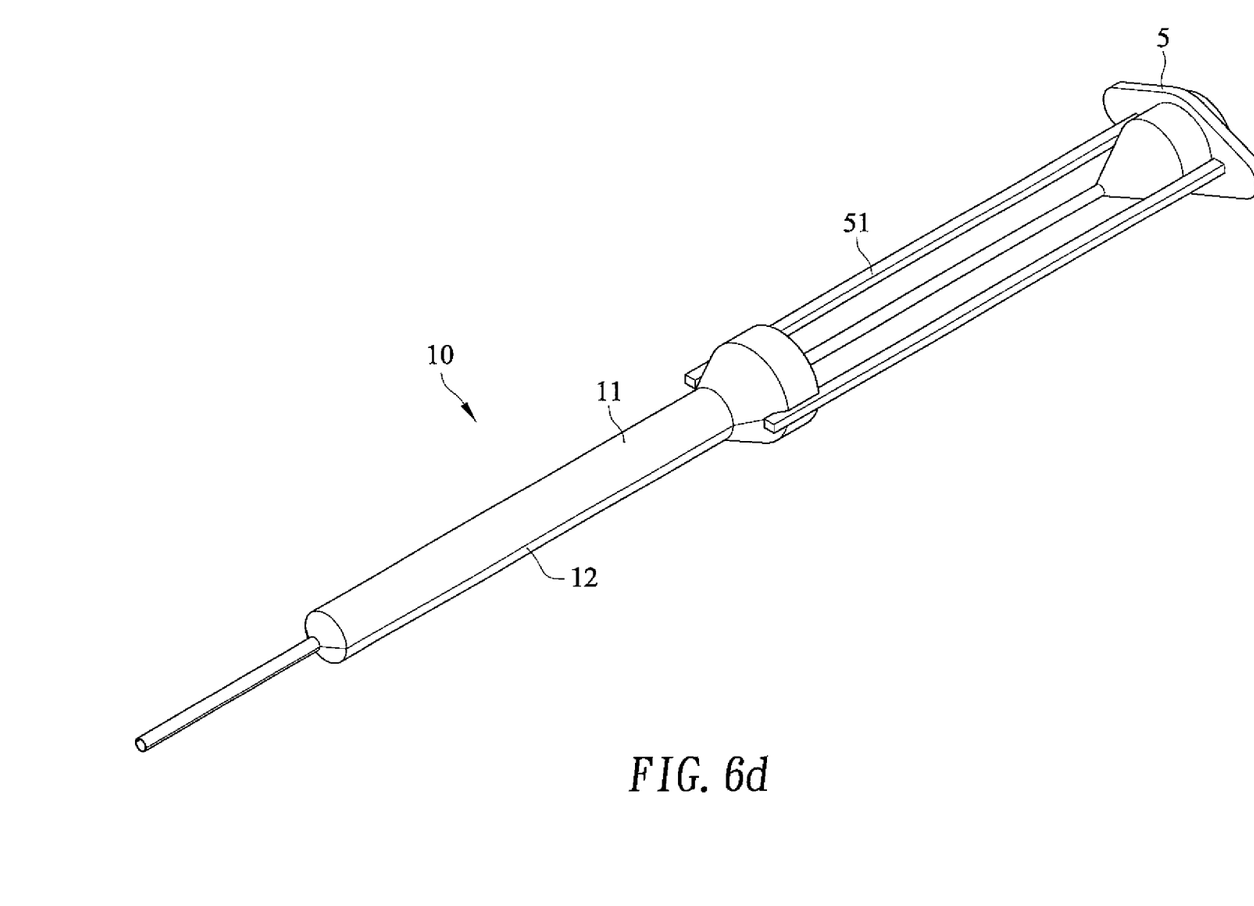

A GDS constructed according to a second preferred embodiment of the present invention is shown in FIG. 4a to FIG. 4d, which comprises an optional component, a sucking plunger 4, for sucking liquid (e.g. blood) into the divided tube 10 to wet the porous granules (not shown in FIGS. 4a-4d) filled therein. In this embodiment, the divided tube 10 has a female half shell 11 and a male half shell 12, wherein the former is provided with a ring structure 13 and two grooves 14 and the latter is provided with two pins 15 corresponding to the two grooves 14 to facilitate the coupling thereof and sliding movement relatively to each other after the coupling. The perforated cap 3 and the plunger 5 are similar to those described in the first preferred embodiment shown in FIGS. 3a and 3b. The granules filled in the longitudinal channel in the divided tube 10 will be stopped by the plunger 5 while the two half shells 11 and 12 of the divided tube 10 are withdrawn alternately, so that the filled granules are exposed gradually from the divided tube 10, falling therefrom due to gravity and/or movement of the divided tube 10. The alternate withdrawing is continued until all the filled granules in the divided tube 10 are delivered, and a front end of the plunger 5 would appear from the longitudinal channel of the divided tube as shown in FIG. 4c.

A GDS constructed according to a third preferred embodiment of the present invention is shown in FIG. 5a to FIG. 5d, which comprises a plunger 5, a perforated cap (not shown in the drawings), and a divided tube 10 composed of a female half shell 11 and a male half shell 12, wherein the former is provided with a ring structure 13 and two pins 15 and the latter is provided with two grooves 14 corresponding to the two pins 15, similar to those of the second preferred embodiment shown in FIGS. 4a to 4d. However, in this embodiment, the divided tube 10 has a rectangular channel formed by the coupling of the female half shell 11 and the male half shell 12, and the plunger has a front end having a rectangular cross-section corresponding to the rectangular channel. The female half shell 11 and the male half shell 12 are further provided with oval recesses on their outer surfaces having a size and a span for ease of the gripping by human finger tips. The plunger 5 is further provided with two opposite arms 51 which have an arcuate cross-section matching the cylindrical divided tube 10, whereby the coupling of the female half shell 11 and the male half shell 12 can be improved, and an operator can hold the plunger 5 more easily.

A GDS constructed according to a fourth preferred embodiment of the present invention is shown in FIG. 6a to FIG. 6d, which comprises a plunger 5, a perforated cap (not shown in the drawings), and a divided tube 10 composed of a female half shell 11 and a male half shell 12, similar to those of the third preferred embodiment shown in FIGS. 5a to 5d. However, in this embodiment, the divided tube 10 has a circular channel formed by the coupling of the female half shell 11 and the male half shell 12, and the plunger 5 has a front end having a circular cross-section corresponding to the circular channel. The female half shell 11 and the male half shell 12 are respectively provided with wedge-shaped grooves 14 and wedge-shaped pins 15, so that the female half shell 11 and the male half shell 12 are coupled by sliding the wedge-shaped pins 15 into the wedge-shaped grooves 14, and thus the ring structure provided on the female half shell of the third embodiment shown in FIGS. 5a to 5d is omitted in this fourth embodiment of the present invention. Moreover, the plunger 5 is provided with two opposite arms 51 which have a rectangular cross-section, and the divided tube 10 after being coupled would form two opposite indentations 52 on a flange thereof to slidably receive the two opposite arms 51.

Figure 7A:
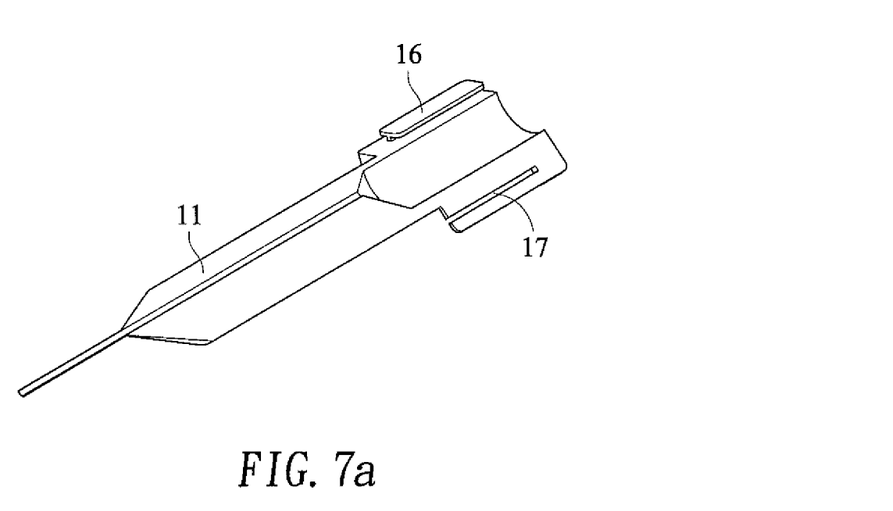
FIG. 7a to FIG. 7c are perspective views showing a GDS constructed according to a fifth preferred embodiment of the present invention.
Figure 7B:
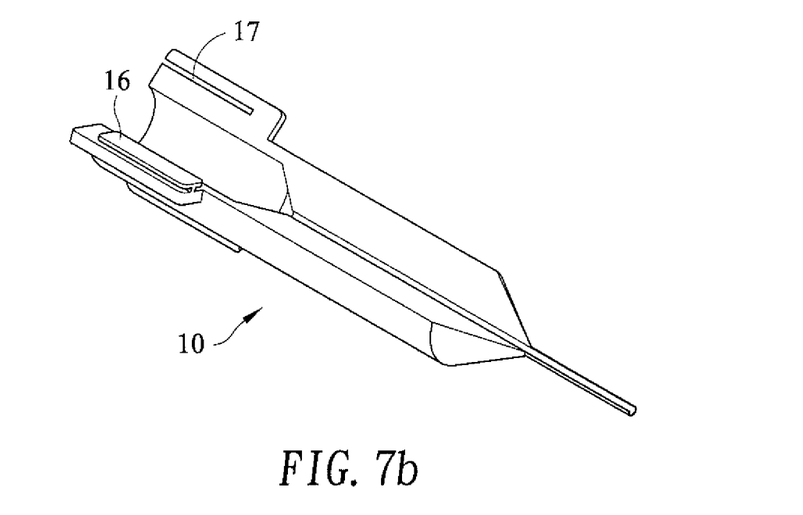
Figure 7C:
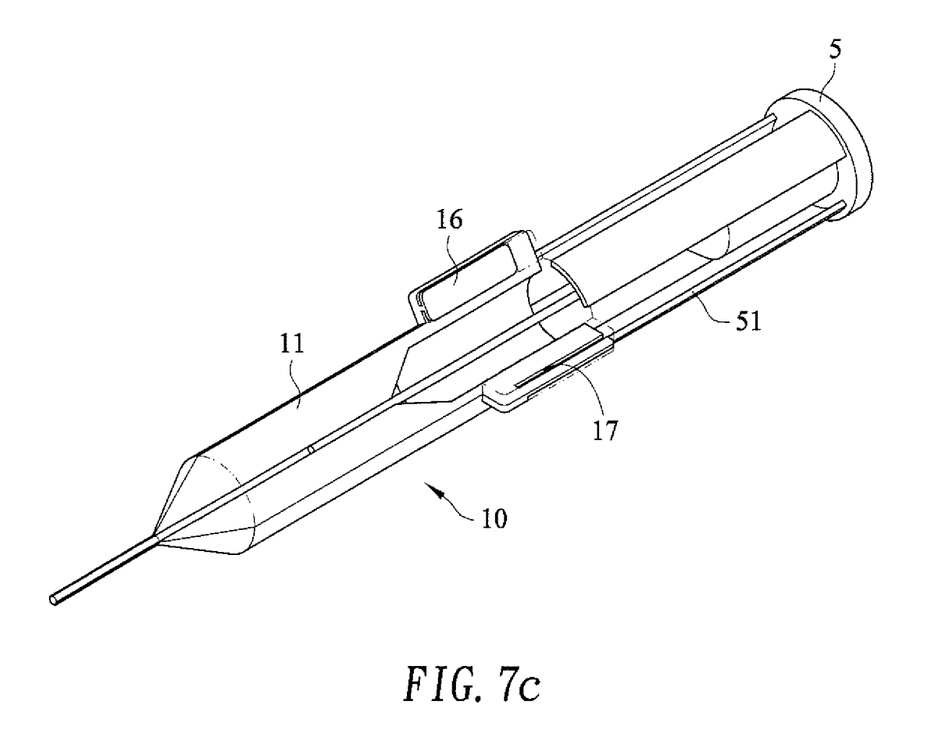

A GDS constructed according to a fifth preferred embodiment of the present invention is shown in FIG. 7a to FIG. 7c, which comprises a divided tube 10 composed of three ⅓ shells 11, a plunger 5, and a perforated cap (not shown in the drawings). In this embodiment, each of the ⅓ shells is provided with a T-shaped protrusion 16 and a longitudinal slit 17, so that they can be engaged with one another to form a divided tube 10, wherein the third ⅓ shell 11 as shown in FIG. 7a imagined as transparent is coupled to the two ⅓ shells 11 which has been engaged to each other. The plunger 5 in this embodiment is similar to that shown in FIGS. 5a to 5d, except that the opposite arms 51 shown in FIGS. 5a to 5d are replaced with three arms 51 separated with an angle of 120 degrees between any two adjacent arms 51.

Figure 8A:
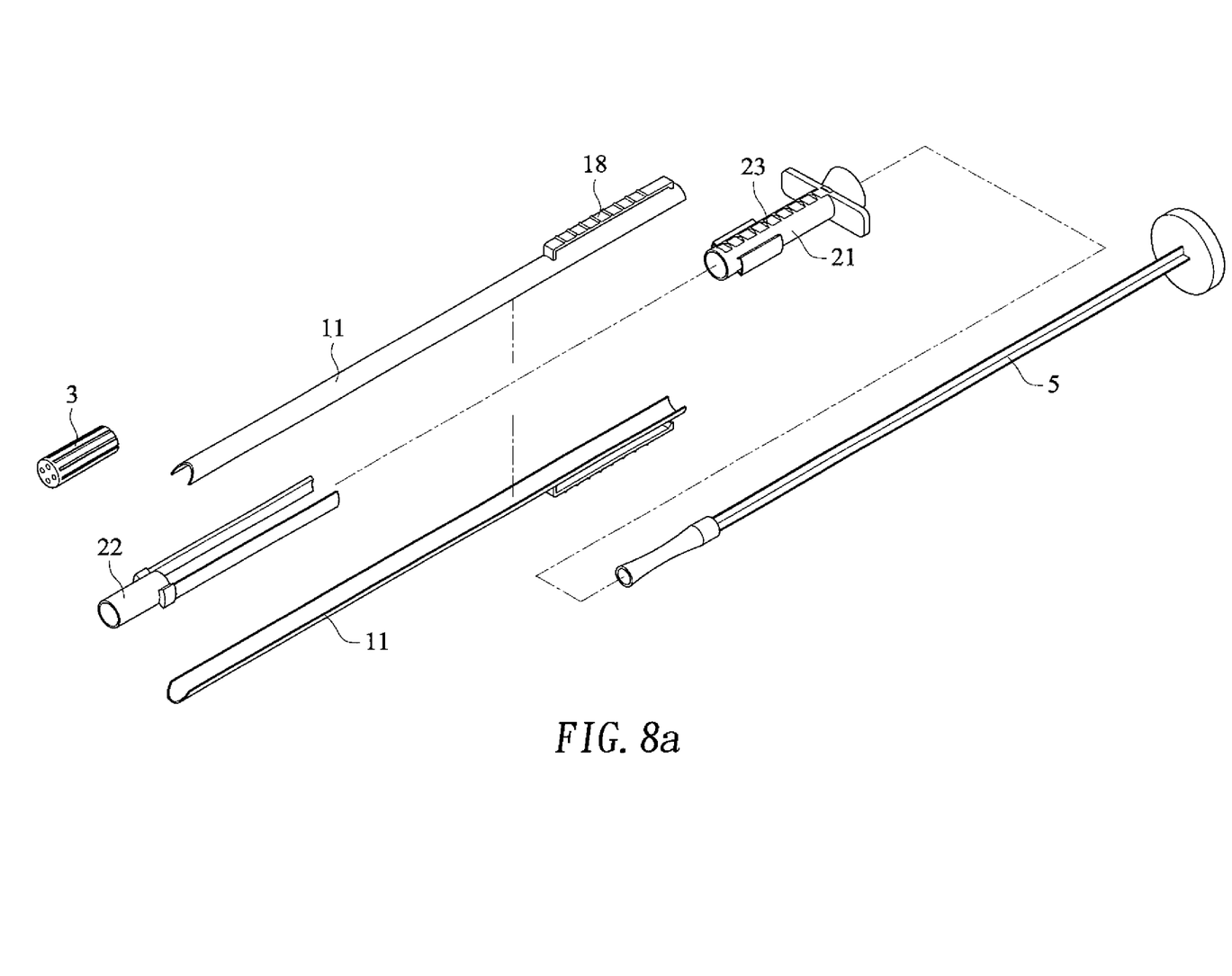
FIG. 8a to FIG. 8d are perspective views showing a GDS constructed according to a sixth preferred embodiment of the present invention.
Figure 8B:
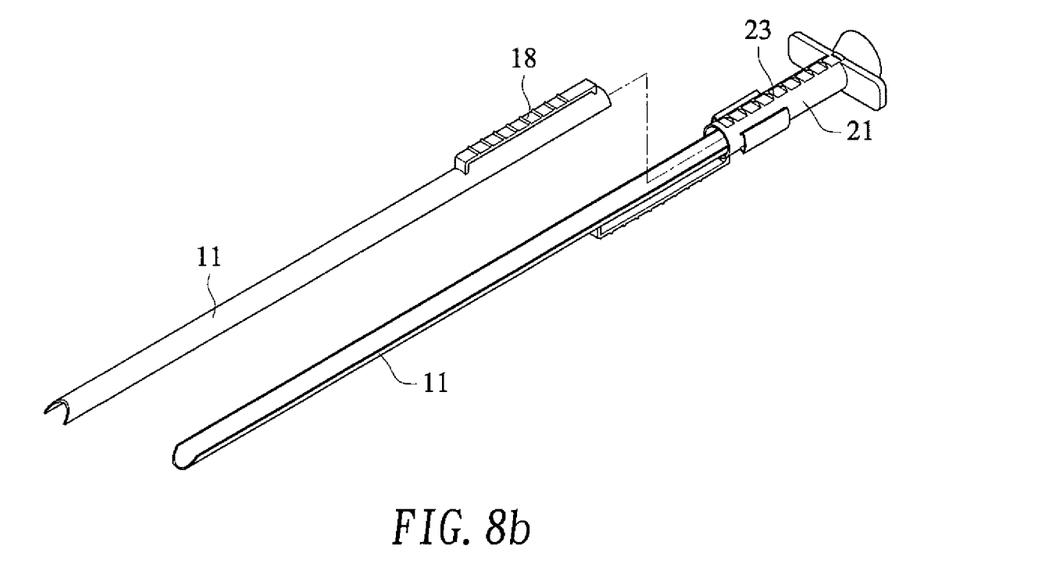
Figure 8C:
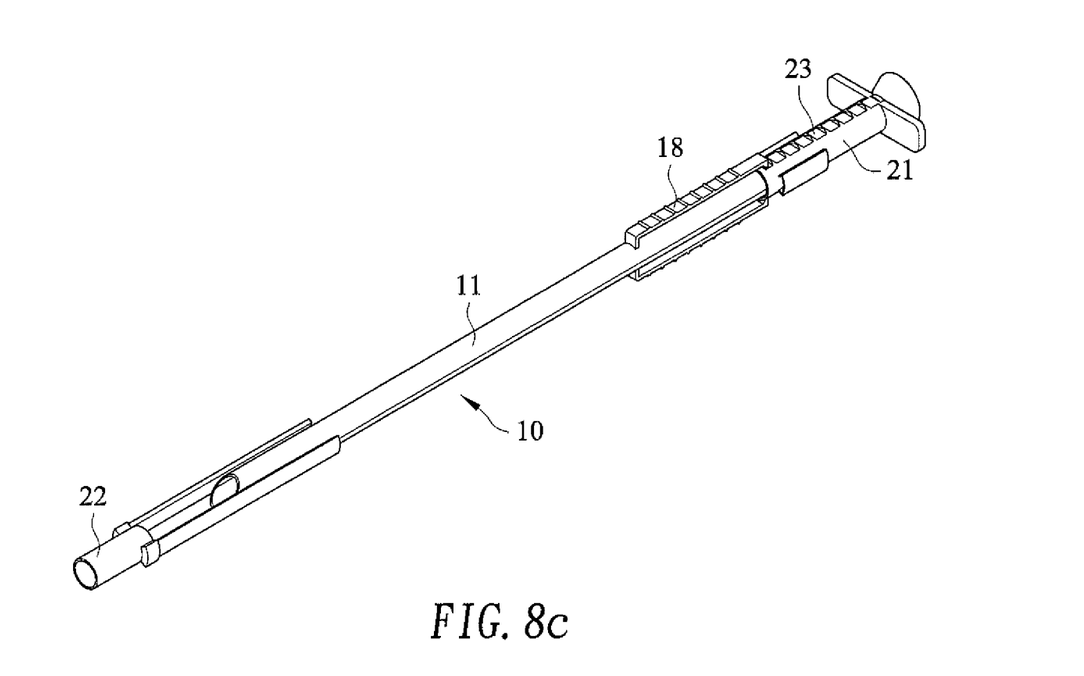
Figure 8D:
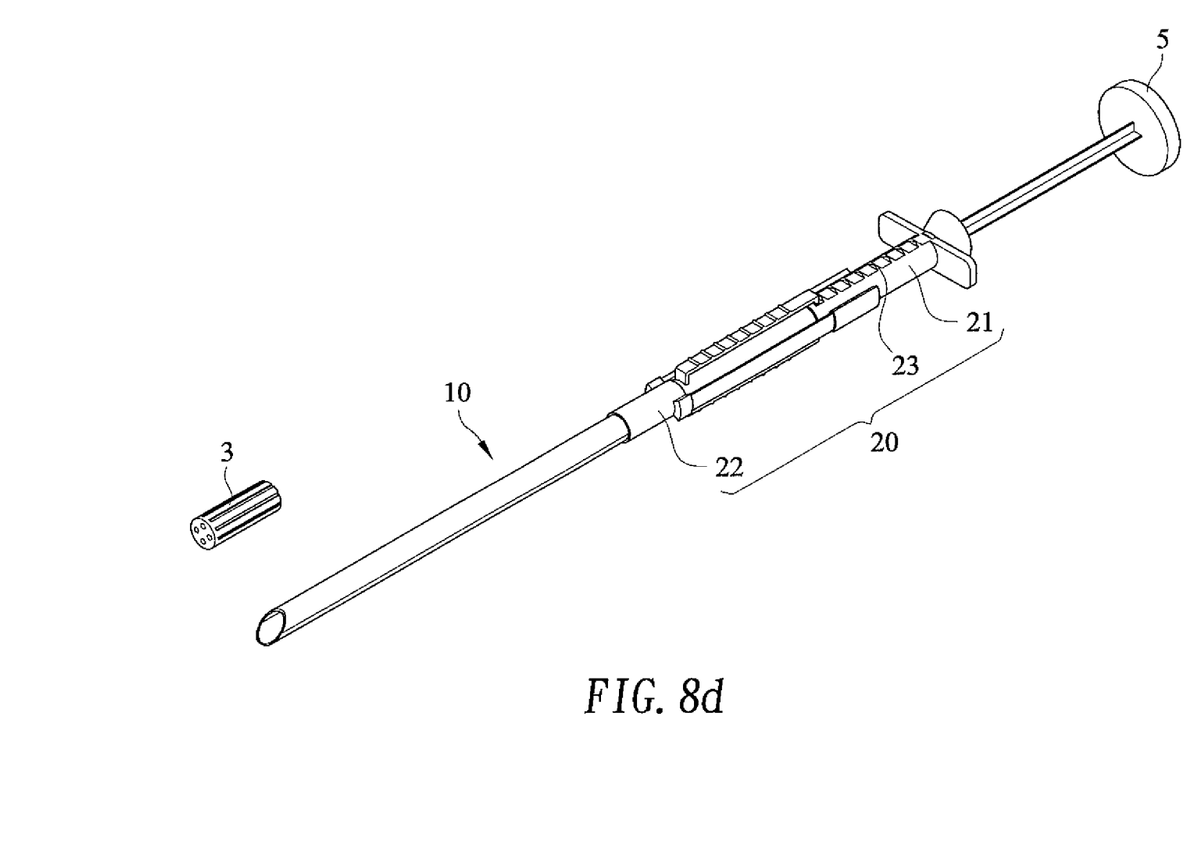

A GDS constructed according to a sixth preferred embodiment of the present invention is shown in FIG. 8a to FIG. 8d, which comprises two half shells 11; a plunger 5, a perforated cap 3, and a holder 20. As shown in FIGS. 8b and 8c, the half shell 11 is provided with an elastic clip 18 on an outer surface near a proximal end thereof. The holder 20 has an upper part 21 and a lower part 22. The upper part is provided with a series of parallel detents 23 corresponding to said elastic clip 18. A proximal end of the half shell 11 is slidably received in a central hole of the upper part 21 with the elastic clip 18 being able to releasably engaged with the detents 23 one-by-one, and the two half shells 11 are coupled to form a divided tube 10. The lower part 22 of the holder 20 is then put on the divided tube 10 from a distal end thereof. The lower part 22 of the holder 20 will contact the upper part 21 of the holder 20, and then the plunger 5 is then inserted into a longitudinal channel formed in the divided tube 10 to complete the assembly of the GDS as shown in FIG. 8d.

Figure 9A:
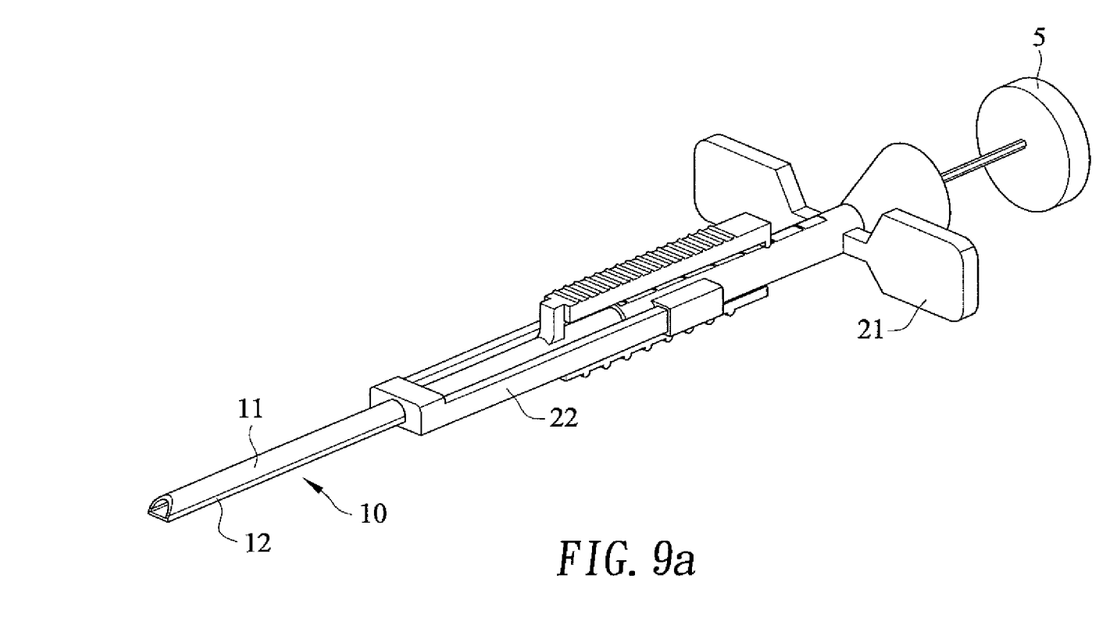
FIG. 9a and FIG. 9b are perspective and planar views showing a GDS constructed according to a seventh preferred embodiment of the present invention.
Figure 9B:
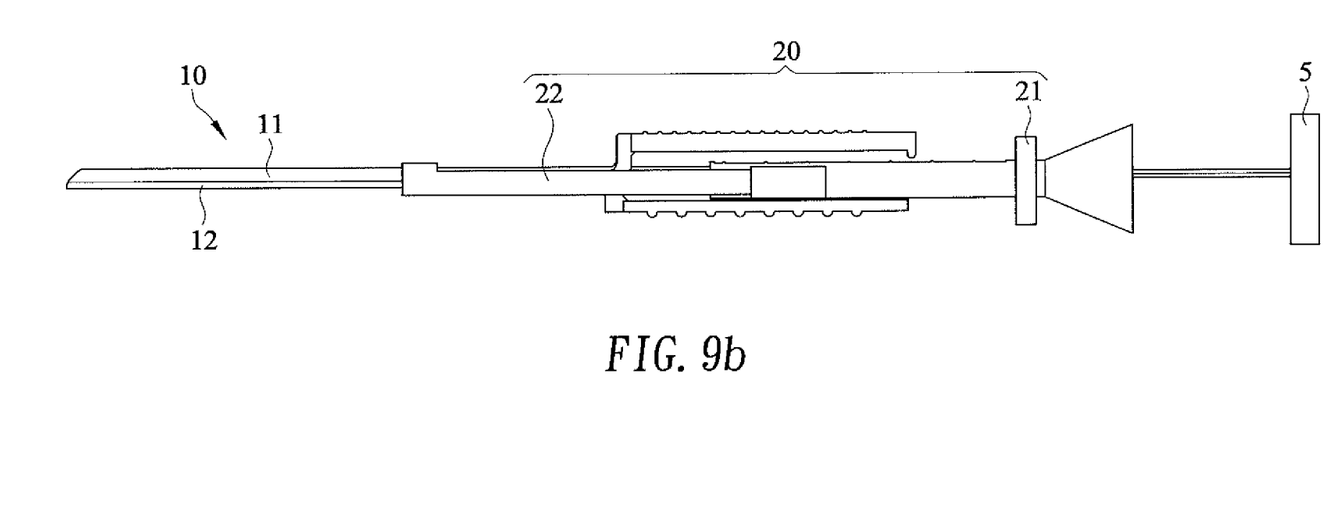

A GDS constructed according to a seventh preferred embodiment of the present invention is shown in FIGS. 9a and 9b, comprising a plunger 5, a perforated cap (not shown in the drawings), a divided tube 10, and a holder 20 having an upper part 21 and a lower part 22, which is similar to the sixth preferred embodiment of the present invention shown in FIGS. 8a to 8d but has a different cross-sectional shape in the divided tube 10. In this embodiment, the divided tube 10 is formed by coupling a semi-circular top shell 11 with a flat bottom shell 12, so that a longitudinal channel having a semi-circular cross section is formed in the divided tube 10, allowing an insertion of the divided tube 10 into a semi-circular cavity, which may be useful in a "sinus lift" surgery.

As it can be understood from the embodiments of the present invention thus described that the granules to be delivered through a tube, and in particular a thin tube, are not pushed through the tube, but remain substantially still with the tube sliding thereon. It is apparent that the design of the GDS of the present invention is particularly suitable for delivering low strength, highly porous granules (for example 80% porosity) through a thin tube, and thus into a small cavity. The primary difference between the GDS of the present invention and a regular syringe is that the GDS of the present invention does not "push" granules forward in the tube. The plunger in the GDS of the present invention is mainly for "holding" the granules in position. The GDS of the present invention "slides" granules into a cavity, while the regular syringe "push" granules into the cavity. For strong, solid granules, the regular syringe might be able to do the delivery job. However, for weak, highly porous granules, the "push" motion of the regular syringe can easily crush the granules into powder before they reach the exit of the syringe.

The invention claimed is:

1. A method of delivering granules into a space comprising the following steps:
   a) preparing a granule delivery system including a plunger and a divided tube, wherein the divided tube comprises two or more partial shells which are adapted to be coupled to each other, so that a longitudinal channel is formed in the divided tube, each of the partial shell is able to move longitudinally in relation to the other, and said plunger is adapted to be inserted into said longitudinal channel, when said two or more partial shells are coupled to each other;
   b) introducing granules into the longitudinal channel formed in the divided tube;
   c) inserting the plunger into the channel of the divided tube to an extent so that the plunger contacts the granules; and
   d) withdrawing said two or more partial shells at the same time or one-by-one to expose the granules from the divided tube.

2. The method of claim 1 wherein the granule delivery system further includes a holder, the divided tube is adapted to be slidably held by said holder, and the partial shells of the divided tube held by said holder are able to move longitudinally in relation to said holder.

3. The method of claim 2 further comprising an engaging means for allowing the longitudinal movement between the partial shells and the holder only in one direction.

4. The method of claim 3, wherein said engaging means comprises an elastic clip provided on each of said partial shells, and a series of parallel detents corresponding to said elastic clip provided on the holder at a regular interval longitudinally, so that the elastic clip is ratchetingly engaged with the series of parallel detents.

5. The method of claim 1 wherein said two or more partial shells are two half shells.

6. The method of claim 1 wherein said two or more partial shells are two half shells.

7. The method of claim 1 further comprising granules adapted to be introduced into the longitudinal channel.

8. The method of claim 1 further comprising repeating the withdrawing in step d), so that more granules in the divided tube are exposed from the divided tube.

9. The method of claim 1 further comprising e) moving the divided tube so that the divided tube is separated from the exposed granules.

* * * * *